(12) United States Patent
Russell

(10) Patent No.: US 12,138,330 B2
(45) Date of Patent: *Nov. 12, 2024

(54) HAIR COLORING MODIFICATION ADDITIVE AND RELATED METHODS

(71) Applicant: PWAI, LLC, Salem, MA (US)

(72) Inventor: Marsha A. Russell, Beverly, MA (US)

(73) Assignee: PWAI, LLC, Salem, MA (US)

( * ) Notice: Subject to any disclaimer, the term of this patent is extended or adjusted under 35 U.S.C. 154(b) by 34 days.

This patent is subject to a terminal disclaimer.

(21) Appl. No.: 17/918,094

(22) PCT Filed: Apr. 11, 2021

(86) PCT No.: PCT/US2021/026764
§ 371 (c)(1),
(2) Date: Oct. 10, 2022

(87) PCT Pub. No.: WO2021/211393
PCT Pub. Date: Oct. 21, 2021

(65) Prior Publication Data
US 2023/0139620 A1 May 4, 2023

Related U.S. Application Data

(60) Provisional application No. 63/008,794, filed on Apr. 12, 2020.

(51) Int. Cl.
*A61Q 5/10* (2006.01)
*A61K 8/04* (2006.01)

(52) U.S. Cl.
CPC ............... *A61K 8/044* (2013.01); *A61Q 5/10* (2013.01); *A61K 2800/882* (2013.01)

(58) Field of Classification Search
CPC .... A61K 8/044; A61K 2800/882; A61K 8/18; A61K 2800/805; A61Q 5/10
USPC .............................................................. 8/405
See application file for complete search history.

(56) References Cited

U.S. PATENT DOCUMENTS

| | | | | |
|---|---|---|---|---|
| 6,461,391 | B1 * | 10/2002 | Lim ..................... | C07D 207/14 8/405 |
| 6,589,295 | B2 * | 7/2003 | Lim ..................... | C07C 215/78 564/336 |
| 7,081,140 | B2 * | 7/2006 | Knuebel .............. | C07D 233/56 8/405 |
| 9,283,158 | B2 * | 3/2016 | Goutsis .................... | A61Q 5/10 |
| 11,123,281 | B2 * | 9/2021 | Russell .................... | A61K 8/73 |
| 2002/0100126 | A1 * | 8/2002 | Lim ..................... | A61K 8/4926 8/408 |
| 2002/0100127 | A1 * | 8/2002 | Lim ..................... | C07C 275/40 8/408 |

(Continued)

*Primary Examiner* — Eisa B Elhilo
(74) *Attorney, Agent, or Firm* — Rosenberg, Klein & Lee

(57) ABSTRACT

An additive is disclosed for use with existing hair coloring products that combines multiple hair dye sources and classifications to create a single precise color tone on demand. The additive salvages chemical parts from existing hair coloring products to create a multitude of new hair coloring options. The additive perfects the dye diffusion process using physics, electrochemical technology and chemical screening technology. The resultant additive mixed with an existing hair product solves many of the problems within the hair coloring industry and enhances safety through lower toxicity.

36 Claims, 5 Drawing Sheets

(56) References Cited

U.S. PATENT DOCUMENTS

2002/0108187 A1\* 8/2002 Lim .................... C07D 295/13
8/405

\* cited by examiner

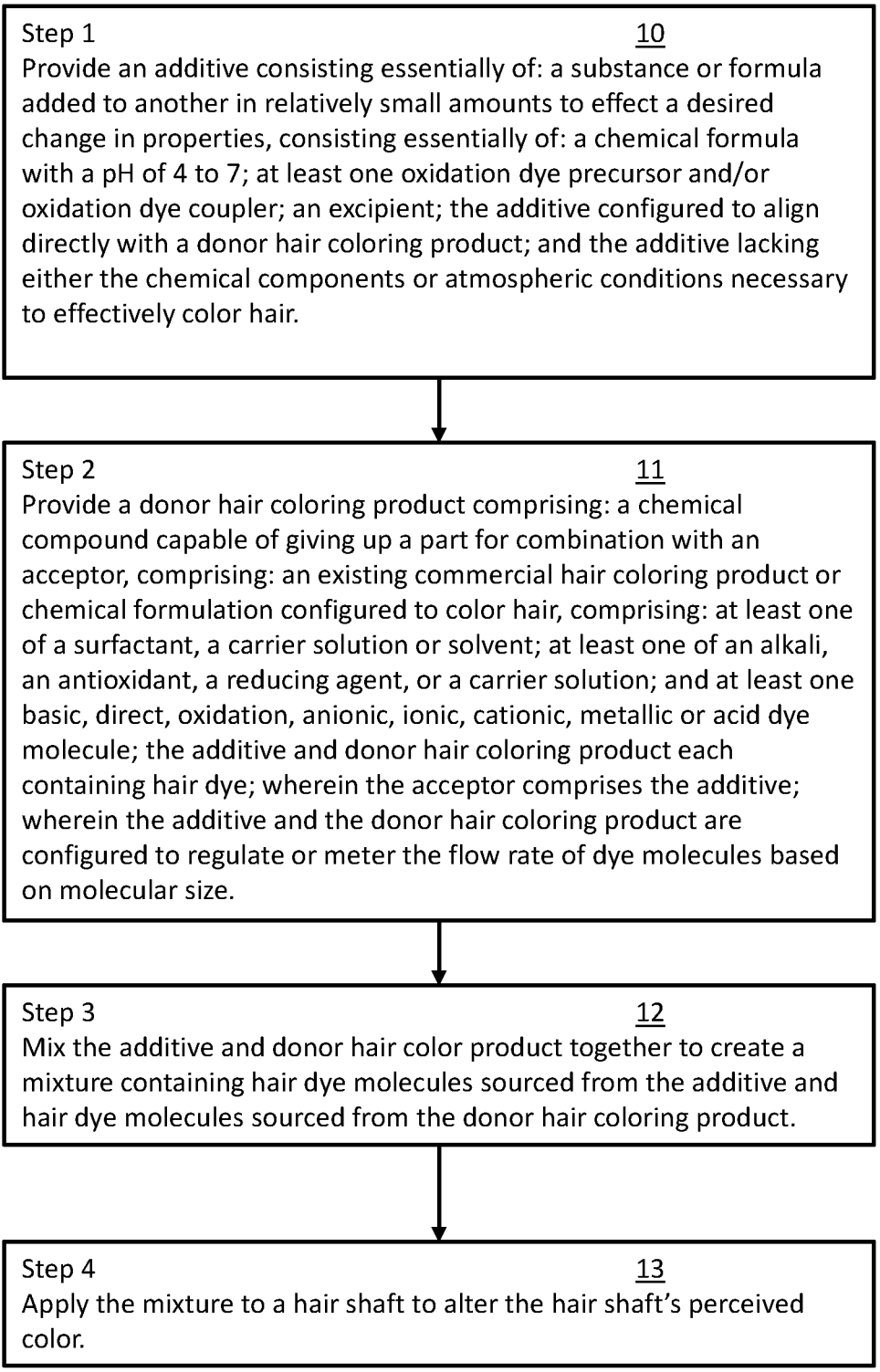

FIG. 2

| Step 3a | 14 |

Add an oxidizer to the mixture prior to applying the mixture to the hair shaft.

| Step 3b | 15 |

Generate a chemical screen or matrix in the mixture to block or meter hair dye molecules and to place them within the hair shaft in order of increasing molecular size.

| Step 4 | 13 |

Step 4 can further include coloring the hair, using the mixture, to utilize three sources of color: the hair dye molecules of the additive, the hair dye molecules of the donor hair product and the melanin or residual dyes from the existing hair shaft to generate a precise hair color tone.

| Step 4a | 16 |

Encapsulate toxic residues, through the mixture, after the hair coloring process is complete.

| Step 2a | 17 |

Collect data comprising:
- the condition of a client's hair;
- the client's current color shade;
- prior hair coloring services received by the client;
- known allergies of the client;
- the amount of gray hair in the client's hair; and
- the final expected color shade desired by the client.

Use the data collected to select a donor hair coloring product. Assigning each piece of data a number or identifying mark; and use the data collected and the selected donor hair coloring product to determine the additive and the amount of the additive needed to align with the donor hair coloring product using a mathematical formula.

FIG. 3A

| Step 1                                                                               20 |
|---|
| Provide an additive consisting essentially of: a substance or formula added to another in relatively small amounts to effect a desired change in properties, consisting essentially of: a chemical formula with a pH of 4 to 7; at least one oxidation dye precursor and/or oxidation dye coupler; an excipient; the additive configured to align directly with a donor hair coloring product; and the additive lacking either the chemical components or atmospheric conditions necessary to effectively color hair. |

| Step 2                                                                               21 |
|---|
| Provide a donor hair coloring product comprising: a chemical compound capable of giving up a part for combination with an acceptor, comprising: an existing commercial hair coloring product or chemical formulation configured to color hair, comprising: at least one of a surfactant, a carrier solution or solvent; at least one of an alkali, an antioxidant, a reducing agent, or a carrier solution; and at least one basic, direct, oxidation, anionic, ionic, cationic, metallic or acid dye molecule; the additive and donor hair coloring product each containing hair dye; wherein the acceptor comprises the additive; wherein the additive and the donor hair coloring product are configured to regulate or meter the flow rate of dye molecules based on molecular size. |

| Step 3                                                                               22 |
|---|
| Blend the additive and donor hair coloring product to create a mixture, wherein the mixture contains a ratio of the active component of the additive to the donor hair coloring product of less than 3:20 by volume or weight. |

| Step 4                                                                               23 |
|---|
| The oxidation dyes precursors and oxidation dye couplers of the additive form at least single nuclear indo dyes. |

| Step 5                                                                               24 |
|---|
| Create, in the mixture, chemical screens ranging from 200,000u to 800,000u in molecular mass and configured to encapsulate and meter the flow rate of hair dye molecules over 6 angstrom. |

HAIR COLORING MODIFICATION ADDITIVE AND RELATED METHODS

CROSS REFERENCE TO RELATED APPLICATIONS

The present application is an international patent application (filed via the Patent Cooperation Treaty) claiming priority to U.S. Provisional Patent Application No. 63/008,794 filed Apr. 12, 2020, which is hereby incorporated by reference in its entirety.

BACKGROUND

1. Field

The present disclosure relates to hair dye formulations, specifically to a hair color additive to modify existing hair dye formulations to produce precise color tones.

2. Discussion of Prior Art

The modern-day human hair coloring industry is growing at a rapid pace. It extends from the youth seeking personalized expression up to the aging population wanting to color grey hair. Much of this technology is based off discoveries made over 100 years ago. Despite all the years that have passed very little progress has been made with regard to advancing on this founding technology.

The process of coloring hair (keratin fibers) requires chemically or naturally dying the physical structure of the hair shaft. The placement and types of dyes used directly correlate to the quality level of the dyeing service performed. Commercial hair coloring products consist of chemical blends or chemical formulations that work in harmony to achieve a desired tonal change. These chemical formulations differ based on a client's affordability, expected durability and color tonal choice.

There are many hair coloring products to choose from and they range from temporary to permanent coloring products. Manufacturers often struggle in producing these products because they need to balance effective coloring results with ease of use and affordability. Hair colorists are not chemist so manufacturers must create these hair coloring formulas in a manner so that a hair colorist can apply them correctly and safely with a basic skill set.

This scenario forces manufacturers to create chemical formulas that take all the guesswork and science out of the hair coloring process. The result is most commercial hair coloring products are a blend of multiple chemicals that are packaged together and sold as ready-to-apply single units or kits.

The dyes used in the production of hair color formulas are very sensitive and prone to alteration by their surrounding atmosphere. Hair dyes usually make up the smallest proportion by volume of a typical hair color formulation. In a perfect world we would deliver these dyes in their rawest and most pure form but because of their small physical size they can't be handled or delivered correctly by a common hair colorist.

Manufacturers are forced to create hair coloring formulas that combine many chemical ingredients such as water, surfactants, stabilizers, antioxidants, alkali, emulsions, excipients and dyes. Most of these chemical ingredients are used to shelter and deliver the hair dye in a precise manner while others target and prepare the hair shaft for accepting the color.

Hair color chemical formulations are unstable and every effort should be made to keep them in an inactive state but in most cases the stabilizing chemicals used just prolong the process of activation and contamination. Most hair coloring products have a shelve life that is not shared with the consumer. This shelf life is very important and particularly vital when oxidation dyes are present.

Premature contamination is the number one reason many hair dye products transform over time into different formulas than intended. This transformation process actually creates a mutation of the original chemical formulation, so it behaves in a different manner than intended and some become toxic over time. As these hair coloring formulas mutate over time, they lose their effectiveness as hair colors. Hair colorists find that they need to use more and more of the same hair coloring formulation as it ages thus pushing them into a toxic position for both the client and applicator.

The mutation process effects the hair dyes directly as it can alter their size or damage them physically. When dye molecules are altered through mutation they perform and diffuse differently and often produce different color tones or hues than originally intended so the further a hair coloring product ages the color tone or hue they produce may also change.

This mutation issue is problematic for a hair colorists. When they begin the hair coloring process, they have a target tonal outcome and select a hair coloring product that meets this need. Unfortunately, the hair color product has mutated over time. When applied by the hair colorist, they realize that the outcome is not heading in the right direction, requiring compensation by adding more hair color or adding additional hair coloring products to offset or override the hair coloring process.

This scenario is commonplace, and it is the primary reason that hair colorists fail to achieve perfect hair coloring results. A particularly negative outcome is when the hair colorist unintentionally forced themselves into a toxic position that surpasses legal limits set by regulatory commissions.

The present invention is directed at overcoming, or at least improving upon, the disadvantages of the prior art.

BRIEF SUMMARY

The present disclosure accomplishes this goal by providing an additive containing oxidation dye precursors and oxidation dye couplers and at least an excipient that chemically alters a donor hair coloring product and its performance to custom build precise color tones within a hair shaft. The additive is an inactive solution that cannot effectively color hair without being mixed with the chemicals included in the donor hair coloring product. Combining the hair dye from the additive, the donor hair coloring product and existing color in the hair shaft, a precise color tone is achieved.

The disclosure includes patentable subject matter directed towards at least the following chemical formulations and methods:

Disclosed herein is an additive directly aligned to a donor hair coloring product, consisting essentially of an additive consisting essentially of: a substance or formula added to another in relatively small amounts to effect a desired change in properties, consisting essentially of: a chemical formula with a pH of 4 to 7, at least one oxidation dye precursor and/or oxidation dye coupler, an excipient, the additive configured to align directly with a donor hair coloring product, and the additive lacking either the chemical components or atmospheric conditions necessary to effectively color hair; wherein the additive is directly aligned with a donor hair coloring product comprising: a chemical compound capable of giving up a part for combination with an acceptor, comprising: an existing commercial hair coloring product or chemical formulation configured to color hair, comprising: at least one of a surfactant, a carrier solution or solvent, at least one of an alkali, an antioxidant, a reducing agent, or a carrier solution; and at least one basic, direct, oxidation, anionic, ionic, cationic, metallic or acid dye molecule, wherein the additive comprises the acceptor, wherein the additive is proportionately aligned to the donor hair coloring product to create a custom hair coloring solution with hair dyes sourced from both the additive and the donor hair coloring product to create a single color shade, and wherein the additive is configured to regulate or meter the flow rate of dye molecules based on molecular size.

The additive can comprise active and/or non-active chemical components wherein the active chemical compounds promote chemical activity and the non-active chemical components deter, prevent or limit chemical activity, and wherein the additive and the donor hair coloring product are performance dependent. The hair coloring solution can comprise a ratio of the active component of the additive to the donor hair coloring product of less than 3:20 by volume or weight. The hair coloring solution can also contain no active component of the additive in a ratio to the donor hair coloring product of greater than 1:10 by volume or weight. The additive can be configured to chemically react with the donor hair coloring product to chemically transform a portion of the additive into chemical screens configured to screen and filter dye molecules based on size. The additive can be configured to chemically use the donor hair coloring product to chemically build at least one excipient into the chemical screens. The additive's excipient, holding a pH of 4-7 and a neutral to anionic charge, can be configured to be mixed with a donor hair coloring product, holding a pH of greater than 7 and a cationic charge, and configured to draw excipients out of the additive and activating them and causing chemical screens to be constructed.

A mixture of the additive and the donor hair coloring product can comprise particulates or granules dispersed evenly throughout the mixture to perform as physical dye chemical screens. The mixture of the additive and the donor hair coloring product can be configured to cause a catalyst to be drawn out of the donor hair coloring product or added to the mixture to grow polymeric chemical screens in one of a fractal, linear or branched chain of repeating units fixed together via chemical links to form a restrictive barrier or matrix. The mixture of the additive and the donor hair coloring product can be configured to direct some hair dye molecules through a transcellular route and other hair dye molecules through an intercellular route through the cuticle layer of human hair. The mixture can be configured to custom build a color tone within a hair shaft based on precise dye placement based on molecular size and tone. The mixture can be configured to use capillary action and/or electrochemical action to draw the hair dye molecules into cortex cavities of the hair shaft in a numerical order based on physical molecular size. The mixture can also be configured to dismantle, salvage and/or encapsulate portions of the donor hair coloring product.

Disclosed herein is a method of coloring hair, steps comprising: providing an additive consisting essentially of: a substance or formula added to another in relatively small amounts to effect a desired change in properties, consisting essentially of: a chemical formula with a pH of 4 to 7; at least one oxidation dye precursor and/or oxidation dye coupler; an excipient; the additive configured to align directly with a donor hair coloring product; and the additive lacking either the chemical components or atmospheric conditions necessary to effectively color hair; providing a donor hair coloring product comprising: a chemical compound capable of giving up a part for combination with an acceptor, comprising: an existing commercial hair coloring product or chemical formulation configured to color hair, comprising: at least one of a surfactant, a carrier solution or solvent; at least one of an alkali, an antioxidant, a reducing agent, or a carrier solution; and at least one basic, direct, oxidation, anionic, ionic, cationic, metallic or acid dye molecule; the additive and donor hair coloring product each containing hair dye; wherein the acceptor comprises the additive; wherein the additive and the donor hair coloring product are configured to regulate or meter the flow rate of dye molecules based on molecular size; mixing the additive and donor hair color product together to create a mixture containing hair dye molecules sourced from the additive and hair dye molecules sourced from the donor hair coloring product; and applying the mixture to a hair shaft to alter the hair shaft's perceived color. The method of coloring hair can include encapsulating toxic residues, through the mixture, after the hair coloring process is complete. The method of coloring hair can include the steps of adding an oxidizer to the mixture prior to applying the mixture to the hair shaft; and coloring the hair, using the mixture, to utilize three sources of color: the hair dye molecules of the additive, the hair dye molecules of the donor hair product and the melanin or residual dyes from the existing hair shaft to generate a precise hair color tone. The method of coloring hair can include the step of generating a chemical screen or matrix in the mixture to block or meter hair dye molecules and to place them within the hair shaft in order of increasing molecular size. In the method of coloring hair, the additive can comprise a containment package comprising a specific dose size of the additive.

The method of coloring hair can also include the following steps, comprising: collecting data comprising: the condition of a client's hair, the client's current color shade, prior hair coloring services received by the client, known allergies of the client, the amount of gray hair in the client's hair, and the final expected color shade desired by the client; using the data collected to select a donor hair coloring product; assigning each piece of data a number or identifying mark; and using the data collected and the selected donor hair coloring product to determine the additive and the amount of the additive needed to align with the donor hair coloring product using a mathematical formula.

In the method of coloring hair, the containment package can contain a dose of the additive corresponding with a specific amount of the donor hair coloring product and an inert gas. The containment package can also contain a dose of additive that is less than 3:20 by volume or weight compared with the aligned donor hair coloring product.

Disclosed herein a method of applying a hair coloring solution to generate a precise color tone, steps comprising: providing an additive consisting essentially of: a substance or formula added to another in relatively small amounts to effect a desired change in properties, consisting essentially of: a chemical formula with a pH of 4 to 7, at least one raw oxidation dye precursor and/or raw oxidation dye coupler, an excipient, the additive configured to align directly with a donor hair coloring product, and the additive lacking either the chemical components or atmospheric conditions necessary to effectively color hair; providing a donor hair coloring product comprising: a chemical compound capable of giving up a part for combination with an acceptor, comprising: an existing commercial hair coloring product or chemical formulation configured to color hair, comprising: at least one of a surfactant, a carrier solution or solvent, at least one of an alkali, an antioxidant, a reducing agent, or a carrier solution, and at least one basic, direct, oxidation, anionic, ionic, cationic, metallic or acid dye molecule; the additive and the donor hair coloring product each comprising hair dye; wherein the acceptor comprises the additive; wherein the additive and the donor hair coloring product are configured to regulate or meter the flow rate of dye molecules based on molecular size; blending the additive and donor hair coloring product to create a mixture, wherein the mixture contains a ratio of the active component of the additive to the donor hair coloring product of less than 3:20 by volume or weight; the oxidation dyes precursors and oxidation dye couplers of the additive forming at least single nuclear indo dyes; creating, in the mixture, chemical screens ranging from 200,000 u to 800,000 u in molecular mass and configured to encapsulate and meter the flow rate of hair dye molecules over 6 angstrom; maintaining a pH level of 6-8 in the mixture;

adding an oxidizer to the mixture; establishing a pH level of neutral to acidic on a client's hair; applying the mixture to a user's hair, the mixture softening the hair shaft, an alkali opening the user's hair cuticle scales to a width of about 10 angstrom or less using a pH level of 7 to 10; dissolving the user's hair intercellular matter and cortical cell walls to reach the pigment cavities using the mixture, dissolving natural melanin and/or residual hair dyes in the hair shaft; forcing the dissolved matter out of the hair shaft, using the mixture; leaving a network of holes, voids and cavities in the hair shaft, and configuring the hair shaft to accept new hair dye; chemically, physically or electronically transporting the mixture, through the chemical screen or filter; reaching the cuticle of the hair shaft and penetrating it using either the transcellular or intercellular route; filling the network of holes, voids and/or cavities in the hair shaft with hair dyes, sourced from both the additive and from the donor hair coloring product; and wherein the filling is configured to occur in a layered effect based on the size of hair dye molecules, passing through the chemical screens.

In the method of generating a precise color tone, the mixture can be configured so that the oxidation dyes precursors and or oxidation dye couplers of the additive dominate a hair dye diffusion process. In the method of generating a precise color tone, the additive's excipient, holding a pH of 4-7 and a neutral to anionic charge, can be mixed with a donor hair coloring product, holding a pH of greater than 7 and a cationic charge, drawing excipients out of the additive and activating them and causing chemical screens to be constructed. In the method of generating a precise color tone, the mixture can be configured to cause a catalyst action for the excipient to grow polymeric chemical screens in one of a fractal, linear or branched chain of repeating units fixed together via chemical links to form a chemical chain or matrix. In the method of generating a precise color tone, the mixture can comprise particulates or granules dispersed evenly throughout the mixture and configured to perform as a physical chemical dye screen.

In the method of generating a precise color tone, the layered effect can provide a precise color tone that comprises the use of A, B and C shades to create a single color tone; wherein each of A, B & C shades can be sourced from the additive dye molecules, the donor hair coloring product dye molecules and a color tone existing in the client's hair prior to the application of the mixture. In the method of generating a precise color shade, the layered effect providing a precise color tone can comprise the step of depositing the A, B & C shades based on dye molecule size, where the additive comprises dye molecules with the lightest shade in the mixture and the donor hair coloring product comprises dye molecules with darker shades in the mixture, causing the light shade additive dye molecules to be deposited before the darker shade donor hair coloring product dye molecules into the hair shaft. In the method of generating a precise color tone, the A, B & C shades can be any combination of hair dyes in the additive, the donor hair coloring product and melanin from the client's hair.

The method of precisely generating a color tone can also comprise steps involving the building and use of chemical screens: encasing and chemically, physically or electronically transporting the mixture comprising: a portion of or the entirety of the additive or donor hair coloring product ingredients through chemical screens; regulating a flow rate of all chemicals included in the mixture, by the density, matrix or mesh opening dimensions of the chemical screens when aligned with the sized molecule intended to pass; regulating and ordering all dye molecules included in the mixture to pass through the chemical screens, based on their molecular size and tone; and allowing dye molecules to diffuse through the cuticle and into the cortex of a hair shaft in a precise numerical order based on molecular sizing. The chemical screens can comprise any single chemical or combination of chemicals that can form a granular or polymeric barrier configured to regulate the passage of other chemicals within a formula or mixture in an orderly fashion, based on molecular size. In the method of generating a precise color tone, the additive's excipient, holding a pH of 4-7 and a neutral to anionic charge, can be mixed with a donor hair coloring product, holding a pH of greater than 7 and a cationic charge, drawing excipients out of the additive and activating them, causing the chemical screens to be constructed. In the method of generating a precise color tone, a catalyst can be drawn out of the donor hair coloring product or added as a separate solvent or surfactant to grow polymeric chemical screens in one of a fractal, linear or branched chain of repeating units fixed together via chemical links to form a chemical screen or matrix. In the method of generating a precise color tone, particulates and/or granules can be dispersed evenly throughout the mixture to create a physical chemical dye molecule screen. The chemical screens can be built using chemicals capable of polymerization. The chemical screens can be built to a size of at least 200,000 u to 800,000 u to prevent their penetration through the cuticle cells or their openings, thus forcing all chemicals to pass through the chemical screens before entering the cortex of the hair shaft.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 1 is a method of applying the additive of this disclosure.

FIG. 2 contains optional method steps that can be used in the method of FIG. 1.

FIGS. 3A & 3B are a method of creating a single-color tone in a hair shaft.

DETAILED DESCRIPTION

Figure 3B:
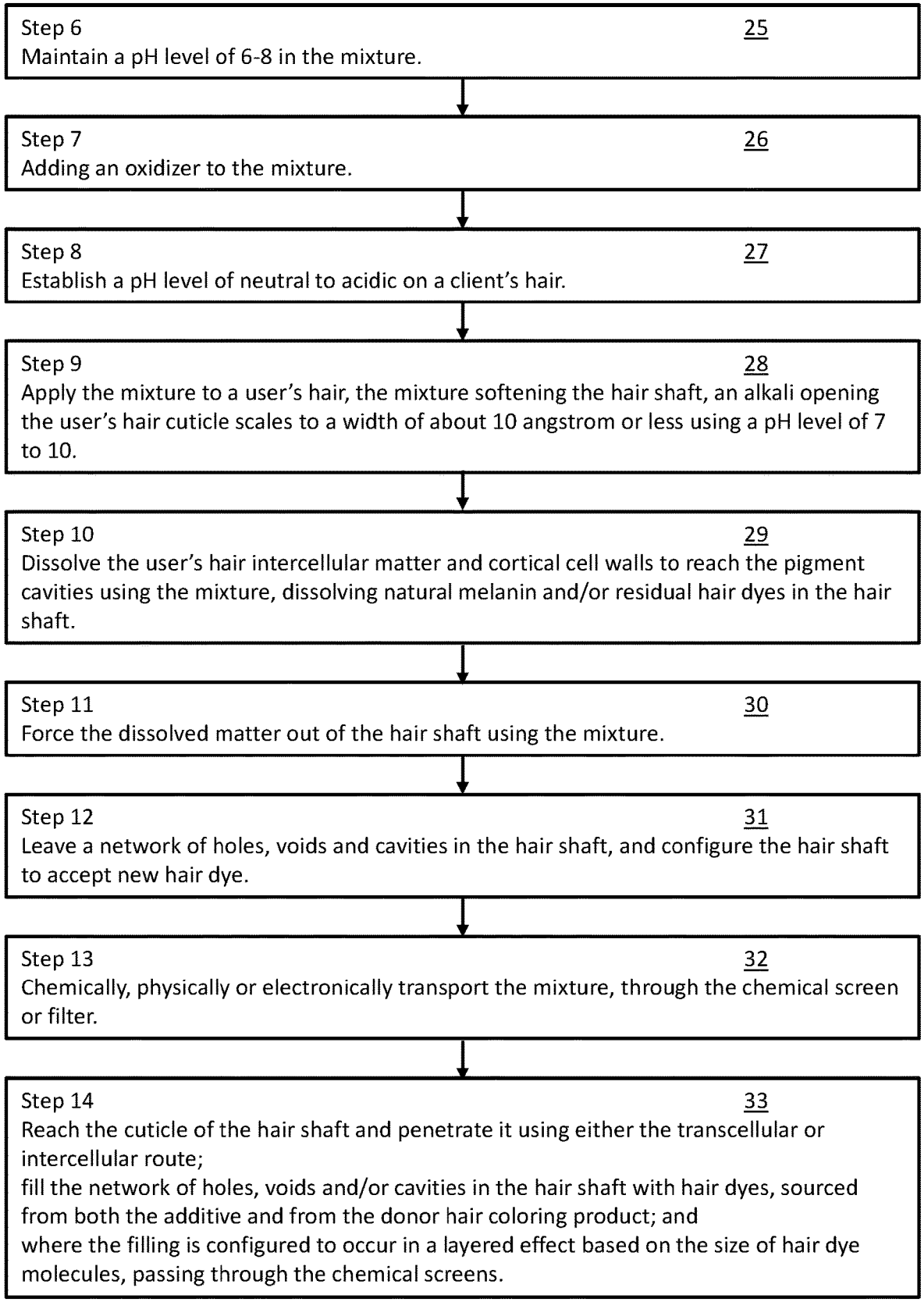

Illustrative embodiments are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure. The additive disclosed herein boasts a variety of inventive features and components that warrant patent protection, both individually and in combination.

The present disclosure relates to an additive developed to enhance existing hair coloring products (hereinafter, "donor (s)") by altering their chemical formulations and performance attributes. The additive salvages chemical components from the donor and combine them with new chemical components found within the additive. Multiple hair dye sources of different classifications are combined to create a single precise hair color tone. The additive and related methods of use take full advantage of the dye diffusion process by combining electrochemical and capillary action to deposit hair dyes within the cortex of the hair shaft in a precise numerical order based on molecular sizing. The outcome is a range of new and existing hair coloring products that are more efficient in coloring hair, which lowers the chemical toxicity of the formulas, making them safer for application.

The present disclosure focuses around enhancing existing hair coloring products by altering their chemical formulations and performance attributes. The disclosed additive salvages chemicals components from these products and combine them with new chemical components found within the additive. Multiple hair dye sources of different classifications can be combined to create a single precise hair color tone. The disclosed additive takes full advantage of the dye diffusion process by combining electrochemical and capillary action to deposit hair dyes within the cortex of the hair shaft in a precise numerical order based on molecular sizing.

A focus of the disclosure was to solve the many hair coloring industry challenges that currently exist, while promoting product safety. The disclosed additive modifies the chemical formulas of existing hair coloring products from the temporary, semi-permanent, demi-permanent, permanent and bleaching classifications to make them safer, while simultaneously producing accurate color tonal effects that out-perform the duration of traditional hair coloring products.

Methods of use accompany the disclosed additive, which include a method of precisely coloring hair and a method of building a custom hair dye shade inside a hair shaft based on precise dye placement based on molecular size and tone.

An additive is, more specifically, a substance added to another in relatively small amounts to effect a desired change in properties. The additive in the present disclosure is used in relatively small amounts compared to the donor. A donor is specifically a compound capable of giving up a part for combination with an acceptor.

The additive is not an effective hair coloring product, but rather a small blend of chemicals intended to change the properties of the donor. The donor gives up chemical parts to the additive acceptor that are missing, thus making it capable of coloring hair effectively. Some parts of the donor are given up and discarded or encapsulated. When blended into a mixture, both the donor and additive work in harmony to create a single premium hair coloring product.

A typical additive formula is a fraction of the donor's volume. There are many variables with regard to the type of donor and the physical structure of the additive so weight is difficult to define. Generally, with all variables the additive active chemicals will represent 15% or less of the total volume of the donor. When applied to a 30 g donor dose the additive active chemical dose will be 5 g or less. This makes the additive to donor ratio less than 3:20 by volume or weight.

The additive contains two or more active chemicals dependent on its intended use and alignment with a donor. There are many possible additive formulas, but in all cases, no single active additive chemical component surpasses 10% of the total volume or weight of the donor.

The focus of the disclosure is on the additive and how it chemically interacts with the donor to create a unique hair coloring solution and used in unique methods of coloring hair.

Additive

The additive is a chemical formulation that includes the chemicals required to solve the many hair coloring industry challenges. The additive is not to be confused as being a hair color product but rather viewed at as being a combination of chemical ingredients designated to complete a portion of the hair coloring process. The additive must be introduced to other chemical ingredients to work or perform as an effective hair coloring product.

A basis of the disclosure is to use chemicals found within the donors and combine them with the additive to ultimately produce a premium hair coloring product from the two separate chemical sources. There are several donor products, and each differ greatly in chemical makeup so the additive must also conform to meet these changing demands. The additive can be adjusted and produced in multiple chemical formulations intended to align with a specific single donor. The combining of these two separate chemical sources is completed by mixing or blending each with one another at time of application.

The additive is designed to be used with a donor to create a hair coloring solution or mixture. The additive disclosed herein is not capable of effectively coloring hair as a stand-alone solution and requires the salvaging and dismantling of components of the donor to create the inventive hair coloring solution and related methods of use.

The additive is a complex chemical formulation made up of both active and non-active chemical ingredients. Each chemical component has a specific purpose while some are directed towards controlling or influencing the chemicals within the physical additive others are intended to control or influence the chemical found within the donor product.

The additive is designed to harness and dominate the dye diffusion process of at least two independent sources of hair dye into the cortex of the hair shaft to create a single precise tone. This process is further complicated when two individual dye sources are blended with a potential third color or dye source. The additive performs a complicated balancing act in controlling the dye diffusion process, which has not previously been successfully achieved.

There are generally two groups of chemicals that make up the additive's chemical formula. The two groups are non-working or non-active and working or active. These two chemical groups differ greatly as one group is intended to defend, protect or deter a chemical reaction (non-working or non-active) whereas the other is intended to promote chemical action or complete a specific duty in an active hair color solution (working or active).

The non-active or non-working chemical portion of the additive is a portion containing a least one or any combination of one or more of the following chemical compounds:

Antioxidant or Inert Medium (table 1)

Reducing Agent (table 2)

Excipient (table 3)

The active or working portion of the additive is a group of chemicals designed to work outside the containment package of the additive. These chemicals target the donor or the hair shaft directly. The active or working chemical portion of the additive is a portion containing a least one or any combination of one or more of the following chemical compounds:

Surfactant (table 4)

Solvent (table 5)

Alkali or Acidifier (table 6)

Oxidation Dye Precursors and Couplers (table 7)

The aforementioned list of non-active or non-working and active or working portions of the additive are further described in Tables 1-7 as noted along side each chemical compound. The above list of non-active or non-working and active or working chemical components can take any form, including but not limited to, a liquid, paste, powder, solid, gas or any combination thereof.

Antioxidant

The additive may include an antioxidant configured to be a stabilizer. An antioxidant can be important to eliminate or limit the amount of oxygen content inside the additive's packaging. Both active and non-active ingredients are present, and the antioxidant assists in creating a favorable protective atmosphere so that all ingredients can combine and remain stable for a duration of time.

A secondary benefit of the antioxidant is to prevent or deter the premature activation of the precursor and coupler, preventing or delaying the forming of indo dyes.

The antioxidant can have a third benefit when blended with a donor/additive product mixture because its existence assists in lowering pH levels within the donor/additive mixture. Possible antioxidants are included as an inclusive list in Table 1.

Inert Gas

An inert gas is similar to an antioxidant but often favored when a physical chemical is not preferred in a chemical formula. The inert gas holds inert properties and can replace the antioxidant but also work in harmony with it so both may be present in or around the additive. Since some inert gases can be considered human safe if used at a proper proportion, they can be used as part of the hair color application process as a chemical assisting tool.

The additive may use a least one or more inert gases to act as an antioxidant or stabilizer. The inert gases can be placed within the sealed additive package during manufacturing or to assist with the manufacturing process.

A secondary benefit of an inert gas can be to control temperature. Carbon Dioxide or Nitrogen may be used to lower the temperature of the additive package, assisting to maintain a preferred −2 to +2 Celsius. Another benefit of an inert gas is to control molecular electrical activity or polarity in both the additive and/or donor/additive mixture.

The inert gases can also be used to control pH levels within the additive, the mixture or the hair shaft either before, during or after a hair coloring service. Possible inert gases are included in an inclusive list of inert medium in Table 1.

Reducing Agent

A reducing agent, also referred to as a reducer, may be used as part of the additive. Reducing agents reduce oxygen content through an electronic redox means. A reducing agent may be used as a stabilizer for the additive.

A secondary effect of a reducing agent can be that of an electronic manipulator, where it holds the ability alter the ionic charge or polarity of ions and change the performance of electrons and protons. This electronic attraction is a benefit if used within the mixture to alter or enhance the dye diffusion rate of flow or diffusion.

Another effect is a reducing agent can be to assist in controlling pH levels whereas it can act as a buffer for maintaining pH in the additive or mixture. Possible examples of reducing agents are included in an inclusive list in Table 2.

Excipient

Excipients are chemicals that can be used as chemical transporters also known as carrier ingredients. Some of the classifications include: antiadherents, binders, coatings, disintegrants, glidants, lubricants and preservatives.

The additive can include one or more excipients to move or transport its chemical components within the mixture. The excipient chosen will greatly depend on the physical makeup of the additive chemicals. Excipients are known for their medical industry benefits as only a food grade chemical, but the current disclosure's use of excipients in a cosmetic product as a new use with the stated benefits.

An excipient can be used in the manufacturing process where it promotes the blending, mixing, flowing of multiple chemicals to create a formula. Excipients can also be used to contain the chemical formula and deliver it in a chemical form such as a tablet, for example.

An excipient can also act as a physical chemical screen or filter. Many excipients such as glidants and antiadherents can be manufactured in very small particulate sizes that do not dissolve, forcing other chemicals to pass through them or around them thus metering them based on molecular size. Binders such as polymers inherently form large molecular chains or matrixes, where the excipients can use spaces between the chain links and areas around the chain as a chemical screen.

An excipient can also encapsulate toxic residues. The large molecular chains or matrixes that are produced by a binder can continue to grow into massive physical size and length. This usually occurs at the end of their work cycle and in our case after the hair coloring process is complete. Binders can encapsulate waste chemicals such as toxic residues and, once encapsulated, they can further dissolve and dismantle them from the inside.

The list of possible excipients is extensive so a sample is provided assuming that a powder physical form for the additive chemicals is chosen. Possible examples of excipients are included in an inclusive list in Table 3.

Surfactant

Surfactants generally reduce surface tension and promote flowability. The classifications are based on the electrical charge of the surfactant thus referring to it as being anionic, cationic, zwitterionic and non-ionic. The additive may include one or more surfactants to assist with blending or combing the chemicals from both the additive and donor to form a mixture and delivering such mixture.

The surfactant can also act as an electronic means to promote flowability through opposite polarity attraction. The additive chemicals can be electrically drawn into the donor to create a mixture and the mixture can then be electrically drawn into the hair shaft.

The surfactant can act as a dismantler of the donor chemical formula. Surfactants can perform as diluents when they behave as emulsifiers or detergents so they can dismantle or dilute other chemicals such as the ones found in donor products. Possible examples of surfactants are included in an inclusive list in Table 4.

Solvent

Solvents are able to dilute a chemical substance and the additive may include a solvent to assist with promoting viscosity and flowability. The consistency of both the additive and additive/donor mixture can be adjusted using a solvent to reach peak performance.

The solvent can also dissolve or dismantle the donor product. Dilution can separate the chemicals within the donor so that they can be isolated and identified. The rate of dilution can allow the donor chemicals to perform in a different manner or in the case of maximum dilution they can be dismantled, neutralized or destroyed. Possible examples of surfactants are included in an inclusive list in Table 5.

Alkali or Acidifier

A chemical element's pH is a standard measurement ranging on a scale of 1-14 whereas 7 pH is considered neutral. Any pH level over 7 is a base and anything under 7 is an acid. An alkali can be used to raise pH levels in a chemical formula and an acidifier can be used to lower pH levels.

The additive chemical formula may include at least one or more or any combination of an alkali or acidifier. They can be used as a pH modifier or regulator. Some donor products do not have an alkali or acidifier and we reserve the right to add one in order to create a more effective hair coloring.

Possible examples of alkalis and acidifiers are included in an inclusive list in Table 6.

Oxidation Dye (Precursors and Couplers)

At the center of the additive invention is its hair dye source known as an oxidation dye. It will be further known as the two parts that form the oxidation dye known as a precursor or coupler. Precursors also known as Intermediates are the primary base of an oxidation dye. They are responsible for most of the chemical performance of the oxidation dye but only produce bland color shades such as dark brown, black and grey. The Coupler chemically reacts with the precursor to fine-tune or transform the color shades produced by the precursor into endless shades of color.

Couplers can be considered dyes, dye parts or other chemicals that act as a coupler for the precursor. In the context of this disclosure, an oxidation dye coupler is considered "any dye, dye part, chemical or formulation directed towards altering the color tone or chemical performance of a precursor."

A sample list of oxidation dye precursors and couplers is included in Table 7, with coupler options in Table 8. The sample list is inclusive and does not bind the disclosure to include any of the specific examples mentioned.

The chemical formulation defining the additive of the invention is held within a separate and isolated container or package, separating it from the donor product. This separation allows each the donor and additive to assume their own identity and chemical makeup with regard to manufacture, sales and marketing.

Packaging the additive's chemical ingredients can require placing them in a container that meets a very strict criteria to prevent contamination. The packaging can be designed to protect the chemical ingredients and stabilize them by preventing contact with the outside environment. The chemicals should be sheltered from sunlight and maintain a certain level of thermal protection. In addition, the package can act as a measuring device and delivery tool that is visually identifiable.

There are many packaging systems capable of meeting all these needs and most are dependent on the physical form of the chemical ingredients placed inside. Liquids can be successfully packaged in bottles, vials or sachets. Powders can be packaged in capsules, bags or sachets and solids can be packaged as tablets. In some cases, the package can include extra space or chambers to allow for mixing multiple chemical ingredients or separating the precursor from the coupler. All the above package forms can be further placed in sealed trays and boxes to add another layer of environmental protection and a commercialized look and feel.

Once a packaging means is selected it can further become more effective by how it is handled and stored. The disclosed additive is intended to be refrigerated until the time of use at an ideal temperature of −2 to +2 Celsius. Refrigerating the additive slows down any electron or proton activity, thus adding to stability.

There are many attributes of the additive and one is its ability to perform as a chemical screen or filter, where the flow rate of all chemicals can be metered based on their molecular size. This is a valuable asset, which can be configured to deposit dye molecules in a particular order during the diffusion process. Excipients are ideal for this task as they can quickly form large molecular chains or a polymeric matrix held together by molecular linkages.

The term "chemical screen" includes any single chemical or combination of chemicals that can form a granular or polymeric barrier that can regulate the passage of other chemicals within a formula or mixture in an orderly fashion based on molecular size. The chemical screen can be constructed by using a chemical that contains a physical particulate of a certain size or produces a certain viscosity. A chemical screen may also be built on demand by using chemicals capable of polymerization.

The additive includes the chemicals required to build a chemical screen. These chemicals can be one or more excipients. These excipients can be sheltered within the additive container and kept in their most inactive chemical state.

The excipient or excipients hold the capacity to form a granular or polymeric chemical screen once blended into an additive and donor mixture. This chemical screen forms a matrix or mesh of openings, where the size of the openings can be adjusted based on their required needs by using or combining different excipients.

A purpose of the chemical screen is to provide a means in which to regulate or meter the passage or flow of hair dye molecules based on their molecular size. Another purpose is to encapsulate unwanted chemicals from within the donor.

When the additive is combined with the donor, a chemical reaction takes place that builds the chemical screen. The additive container maintains a preferred pH of 4-7 and the excipients within the additive hold a neutral to anionic charge. All donor products are higher in pH than the additive and most hold a cationic charge. This difference in pH and ionic charge will draw the excipients out of the additive and activate them, creating a mixture that begins the chemical screen building process.

In the case of particulates or granules, they will be dispersed evenly throughout the additive and the donor mixture. In the case of polymerization, a catalyst is drawn out of the donor or added as a solvent or surfactant from the additive. The polymeric chemical screen then begins to grow in physical size as it forms either fractal, linear or branched chains of repeating units held together by chemical links to ultimately form a matrix.

An intent is to create chemical screens that align directly with the size of the dye molecule intended to pass through its openings. Another intent is to create chemical screens that are prevented from being drawn into the cuticle or cortex of the hair shaft, classifying the chemical screens as surface screens.

Precision in creating a chemical hair dye screen is a significant aspect of this disclosure. The disclosed chemical screens can meter the flow rate of any hair dye molecule over 6 angstrom. Any granule or polymeric matrix also must be larger than 200,000 u (molecular mass) in order to not penetrate the cuticle of the hair shaft.

We hold the ability to create hair dye chemical screens larger by altering the excipients used in the additive formula. Nano technology will be supported to create a family of chemical hair dye screens ranging from 200,000 u to 800,000 u in size.

Donor Hair Product

The donor used in this disclosure can be any type of commercial hair coloring products. Based on their quality, performance and type of hair dye used, existing commercial hair coloring products fall under the following five classifications: Temporary, Semi-Permanent, Demi-Permanent, Permanent and Bleaching.

Temporary

Temporary hair colors are at the lower end of the quality scale and consist of rinses, gels, mousses and sprays. Temporary hair colors last between one to five washes and generally incorporate large structured basic cationic dyes that attach to the outside of the hair shaft. They are held in place by a positive/negative ionic attraction whereas the hair shaft has a natural negative-charge and the cationic dyes are positive. The cationic dyes can last longer than five washes if the hair shaft is etched or damaged as the dye molecules can attach and bond to these hair imperfections.

The hair dyes used in temporary hair colors are generally Food Grade and Synthetic Organic Chemical (FD&C) dyes or Direct Dyes and Basic Cationic Dyes (D&C) and several must be blended in order to get a specific color tone. In some cases, anionic and acid dyes have been used successfully. Generally temporary hair colors maintain a pH (potential Hydrogen) of 5-7.5

A typical temporary hair color formula contains a thickener, surfactant, polymer, buffer, an acid of tartaric, acetic or citric type and cetrimonium chloride. An exemplary formula of a temporary hair coloring solution is: Water, Nonoxynol-9, Hydroxyethylcellulose, Cetrimonium Chloride, Neodol 91-2.5, Citric Acid Trihydrate, Trisodium Phosphate, Acid Violet 43, Direct Red 80, Acid Orange 24, Direct Black 51.

Semi-Permanent

Semi-Permanent hair colors are at the middle of the quality scale and consist of pre-packaged dye formulas that are often matched up with a hair conditioner and sold as a set. Semi-Permanent hair colors last between four to eight washes and generally incorporate smaller structured aromatic amine, amino nitrobenzene or anthraquinone derivative dyes that penetrate the cuticle of the hair shaft and sit within the cortex of the hair shaft. They are held in place by weak polar bonds and since no oxidizer is used, the chemical effects are minimal, so these dye molecules basically float freely within the cortex. The pH level of semipermanent colors is 6-9.

These smaller structured dyes can easily be washed out of the hair shaft because they are free floating so pH control is very important. Hair conditioners are often used to maintain a proper pH of between 4.5-5 on the outside cuticle thus keeping it closed and preventing dye molecules from escaping. The hair dyes used in semi-permanent hair colors are generally HC, Acid or Direct dyes and often as many as 10-18 are blended in order to get a specific color tone.

A typical semi-permanent hair color formula contains a solvent, surfactant, amide, fragrance, acid or alkali. The solvent is often water, glycol or a glycol derivative attended to balance viscosity and pH levels. An exemplary sample formula of a semi-permanent hair coloring composition is: Water, Cocodiethanolamide, Neodol 91-2.5, NaDodecylbenzene Sulfonate, Sodium Lauryl Sulfate, 2-Nitro-p-phenylenediamine, HC Red No. 3, HC Yellow No. 2, HC Blue No. 2.

Demi-Permanent

Demi-Permanent hair colors are actually hybrid colors and combine both the chemical features and performance features of both semi-permanent and permanent hair colors. They are classified as being in the upper middle quality range and considered less toxic than permanent hair colors. They incorporate HC, Acid, Direct and Oxidation Dyes and include an oxidizer.

This hybrid hair coloring product can last up to 20 washes. The key difference is demi-permanent hair coloring products undergo a chemical reaction due to the influence of an oxidizer. This chemical reaction alters the structure of the physical hair shaft so all the semi permanent dyes listed previously can perform in a different manner. Demi-permanent hair colors usually range from 8-10 in pH.

Since demi-permanent hair coloring products can include multiple dye types, their formulas can vary greatly. It must be assumed that a majority of the dyes and chemicals disclosed as semi permanent and oxidation hair colors can be used to create a demi-permanent hair color formula. An exemplary sample formula of a demi-permanent hair coloring composition is: Water, Cocodiethanolamide, Neodol 91-2.5, NaDodecylbenzene Sulfonate, Sodium Lauryl Sulfate, 2-Nitro-p-phenylenediamine, HC Red No. 3, HC Yellow No. 2, HC Blue No. 2. Dodecyl Benzene Sulfonate, Ammonium Hydroxide, Sodium Sulfite, p-Phenylenediamine, o-Aminophenol, p-Aminophenol, 4-Methyl-5-Aminophenol, m-Aminophenol.

Permanent Hair Colors

Permanent Hair Colors are also known as Oxidation Hair Colors and this classification of hair color is considered the highest quality. There are many variables with regard to formulations and application methods but if done correctly, permanent hair colors can last permanently and become resistant to wash out.

The dyes used in permanent hair colors are unique whereas they are built from dye components known as precursors and couplers. We call these dyes Oxidation Dyes because they are greatly influenced by an Oxidizer. Oxygen is the catalyst that sets off a chemical reaction between the precursor and coupler by first reacting with the precursor followed by the coupler. When activated by a catalyst, precursors form active intermediates that condense with couplers and ultimately build di, tri and polynuclear indo dyes.

Oxidation dye precursors are derivatives of aniline and disfunctional ortho, para diamines or aminophenols. Precursors are capable of oxidizing to diminium or quinoniminion ions. When precursors are activated by a catalyst without a coupler present, they produce grey, brown and black shades. Oxidation dye couplers are electron rich aromatic species. Couplers have little or no color but modify the grey, brown and black shades of the precursor to create endless shades of hair colors. The pH levels of permanent hair colors range from 8.5-10.

A typical oxidation dye hair color formula can include surfactants, alkali, reducing agents, water and two, three or more precursor or coupler types to create a precise color tone. An exemplary sample chemical formula of a oxidation dye hair color is: Water, Dodecyl Benzene Sulfonate, Cocodiethanolamide, Neodol 91-2.5, Ammonium Hydroxide, Sodium Sulfite, p-Phenylenediamine, o-Aminophenol, p-Aminophenol, 4-Methyl-5-Aminophenol, m-Aminophenol.

The Oxidizer is the chemical component that acts as a catalyst for the oxidation dye process but does not contribute directly to the shade of the hair color desired. Since the oxidation dyes work hand-in-hand with an oxidizer we will focus some attention on this chemical formulation.

An Oxidizer is any chemical or means that delivers oxygen to the hair color formulation. This is usually done as a separate step and oxidizers are usually kept isolated from the precursor or couplers until the time of application.

The most common oxidizers used are Hydrogen Peroxide, bleach, Peroxymonocarbonate and other optional choices are available such as Peracids, Autoxidation and Air Oxidation of highly electron rich dye precursors. There basically is no limit on what an oxidizer can be, as long as it works in harmony with the hair dye formulation. An exemplary sample hydrogen peroxide formula is: Hydrogen Peroxide, Dodecyl Benzene Sulfonate, Water and Phosphoric Acid.

Bleaching hair colors are considered permanent hair colors because of the drastic chemical reaction that takes place when using them. Bleaching hair damages it structurally and strips it of key proteins and melanin. Bleaching hair colors are very much different than others but considered high quality for a client seeking lighter shades of color.

A typical bleaching color consist of three parts: hair lightener base, the lotion developer and booster powder or accelerator. The lightener base is the primary body of the bleaching hair color and the lotion developer and booster or accelerator are oxidizers or developers. The developer and booster contain high levels of oxidants and often several are present such as Hydrogen Peroxide, Potassium Persulfate and Ammonium Persulfate. Once the three components of a bleaching hair color are mixed together a pH range of 9-12 is often observed.

The lightening base contains the coloring components of a bleach hair color. A typical formula based on volume is Cocodiethanol Amide, Oleic Acid, Dodecyl Benzene Sulfonate, Neodol 91-2.5, Ammonium Hydroxide, Sodium Sulfate, Deionized Water and Hair Dye of any classification.

Donor hair products can include the following inclusive list of chemical components, which can be used in some embodiments of the present disclosure: glycerin, carboxylate, glycol distearate, sodium lauryl sulfate, ascorbic acid, sodium sulfate, ppg-5-celeth-20, dicetyl phosphate, celeth-10-phosphate, behentrimonium, methosulfate, sodium lauroyl sacrosinate, ceteareth-20, propanediol, oleyl alcohol, amodimethicone, cetrimonium chloride, quaternium-91, cetrimonium methosulfate, ppg-3 benzyl ether myrislate, acetamide MEA, ethylhexyl palmitate, panthenol, erythorbic acid, glutamic acid diacetate, propylene glycol, dioleyl phosphate, cocamidopropyl betaine, glyceryl stearate SE, oleth-5-phosphate, linalodol disodium EDTA, cetyl alcohol, stearyl alcohol, oleth-30, ethanolamine, tetrasodium EDTA, bulylene glycol, potassium sorbate, hexadimethrine chloride, ethanolamine, titanium dioxide, acetonitrile, triethylphoshate, glycerol, dimethyl formamide, ethylene glycol monomethylether, diethylene glycol monomethylether.

Dye Shades

Synthetic dyes are produced in many shades and oxidation dyes can be built to mimic most shades. Understanding dye shades begins with a basic concept of color. A color wheel is a full spectrum of all color shades laid out in a circle. Any one single shade chosen from the color wheel is known as a hue.

Basic color shades are any combination of the three primary colors, Red, Yellow and Blue. Secondary colors are a mixture of any two Primary colors. Tertiary colors are a mixture of any Primary color with any Secondary color. Complementary colors are placed opposite on a color wheel and Split Complementary colors are on either side of the Complementary color. Analogous colors are the adjacent color on a color wheel. Monochromatic colors are any of the above color shades modified by a tint or tone.

The hair coloring industry uses a unique charting system to identify levels or shades of hair color. They use a scale of 1-12 whereas 1 represents the darkest hair color shade and 12 represent the lightest hair color shade. A letter or group of letters often follows the number such as 7A whereas A represents an ash, G represents gold and C represents a copper tone so most hair colors are monochromatic colors that are influenced by a tone.

The process of coloring hair often requires blending multiple dye shades with natural melanin found within the hair shaft so some hair colors start out as secondary colors and end up being monochromatic color shades. The hue from a color wheel assumes a white background but when the same hue is applied to hair of a certain color it forms a different hue that is a combination of the base color and hair shade.

The disclosure incorporates many dye types such as anionic, cationic, ionic, oxidation, reactive, metallic, vegetable and acid. Each of these dye molecules are of a different physical size and preform differently when used in the hair coloring process.

The hair shaft holds natural hair color pigments known as melanin and the size and color of these pigments can vary greatly dependent on a person's genetic or ethnic background. In some cases, a person may have colored their hair before, so the hair shaft is holding dye pigments or molecules from a prior hair coloring process. The condition of the physical hair shaft matters greatly as it determines the mechanical means for accepting or rejecting new hair color dyes. Gray hair, for example, is mechanically and physically structured different than young healthy hair, therefore gray hair is the most difficult to color with hair dye.

A key technical feature of the disclosure is a hybrid hair dye (based on the additive and the donor) built on demand within the cortex of the hair shaft from several dyes types and sources. This hybrid hair dye is achieved by using capillary action combined with electrochemical action to draw the hair dye molecules into the cortex cavities of the hair shaft based on physical molecular size where they are allowed to blend and transform into larger molecular structured indo hybrid dyes. Considering all the variables, just getting a single precise hair color dye tone is an important feature of the disclosure, but the disclosure goes even further by depositing the precise hair color dye tone precisely within the pigment cavity of a hair shaft. This disclosure accomplishes these unexpected benefits through the use of electrochemical dye diffusion along with physical molecular sizing and placement.

Physical Structure of Hair

Human hair, also known as keratin fibers, are a complex structure composed of 45.2% Carbon, 27.9% Oxygen, 6.6% Hydrogen, 15.1% Nitrogen and 5.2% Sulphur. Four physical regions make up the structure of human hair: the Mantle, Cuticle, Cortex and Medulla.

The outside layer of the hair shaft, known as the Cuticle, is a scale-like armored covering that protects the inside proteins of the hair shaft from the outside elements. As with most armor, it must move and also remain strong. Flat overlapping cells make up the Cuticle and they are hinged at the root and open at the top end. They take on the physical similarities to scales on a fish or shingles on a roof. Each cuticle cell is approximately 0.5 to 1.0 µm thick and about 45 µm long. The cuticle in human hair is approximately 5 to 10 layers thick. The cuticle cells are made up of four layers: the Epicuticle, A Layer, Exocuticle and the Endocuticle.

The Mantle is a protective fluid layer that covers the outside of the Cuticle. The Mantle is made of oil, salt and water. The primary propose of the Mantle is to maintain the proper pH level of 4.5-5.0 on the outside of hair shaft. At a pH level of 4.5-5.0, the hair shaft is at its maximum shine and strength. The Cuticle scales are closed, thus making the hair shaft smooth to the touch. Simply washing your hair and removing the Mantle can change your hair's pH level, resulting in an immediate change in look and feel. After washing off the Mantle it must be regenerated by the body naturally or by applying conditioning solutions. Unwashed hair is usually the shiniest and strongest due to the presence of a strong Mantle.

Just inside or under the Cuticle is an interwoven body of Keratin cells known as the Cortex. The Cortex is very complicated as it holds many parts and performs many functions. The Cortex is primarily made up of Cortical Cells. These cells are elongated tubes that travel lengthwise within the hair shaft. These cells are about 1-6 µm wide and about 100 µm long. Cortical cells are tubes that hold two key components of the hair shaft: the Pigment Cavities and Macrofibrils.

Pigment Cavities are small elongated cavities that hold color pigment granules and melanin. Each pigment granule is oval or spherical in shape and about 2,000-8000 Angstrom in diameter. These cavities are spread out evenly throughout the Cortical Cell.

Macrofibrils are smaller tubes placed within the larger tubes. Inside these Macrofibrils are the filament protein chains. The chains can be referred to as Polypeptide Chains. The attachment points of the chain are referred to as: Peptide Bonds or End Bonds. There are three types of Bonds: Hydrogen, Salt and Disulfide Bonds. Hydrogen bonds make up the majority and are relatively weak bonds that can be broken by water and reattached by drying the hair. Salt bonds are also weak bonds that require alkaline or increases in pH to break the bond. Disulfide bonds are atomic bonds that are the strongest and provide most of hair's strength. Disulfide bonds are broken only by altering the atomic structure of the hair.

The Cortical Cells are surrounded by Intercellular Matter that is referred to as the "Non-Keratinous Region." This region is filled with cement or glue and a Cell Membrane Complex and is approximately 300-600 Angstrom thick. The cell membrane complex consists of three sublayers. The Delta layer is an intercellular cement that is about 100 Angstrom thick sandwiched between two lipid or fatty cell layers that are about 50 Angstrom thick. This non keratinous region is considered the pathway for hair dye molecules and vital to the dye diffusion process.

The Medulla is placed at the center of the hair shaft. It's considered to be a tube-like feature that runs the length of the hair shaft. Sometimes the tube is shown as broken or spotted and in some cases two medullas are present. The medulla is a vacant tube lacking matter. It is theorized that the medulla is an air space at the center of the hair shaft intended to absorb the effects of expansion and contraction of the physical hair shaft.

Safety Regulations

COLIPA (Comite de Liaison European de Industrie de la Parfumarie de Produits Cosmetiques et de Toilette) and EUCD (EU Cosmetic Directive) and DEPA (Danish Environmental Protection Agency) are European based regulatory commissions that oversee and set safety standards for hair dye products in Europe. The FDA (Food and Drug Administration) is a United States federal department that oversees cosmetic regulations within the United States. Much of the world, including the U.S., adopts COLIPA standards as being the universal regulatory system for cosmetic products.

COLIPA regularly test new and existing hair coloring chemicals to determine if they are safe for use on humans. They produce a list of approved and unapproved chemicals for use in manufacturing hair coloring products and they also set limits on the amount of each approved chemical that is allowed. These safety limits are usually a percentage of total volume of the hair coloring formulation produced.

When the hair color product mutation concept (as described in the Background) is applied to safety standards set by COLIPA, it becomes obvious that the rules have changed. The hair colorist is now applying much more hair color solution in a single application than intended and combining it with additional hair coloring chemicals to correct an undesired outcome.

COLIPA was never set up to address this toxic mess because it's looked at as being a secondary or residual complication created by using the hair color solutions incorrectly. This toxic scenario is very common and hidden under the radar of most product safety commissions so we will bring it to the surface and solve it.

Dye Diffusion Method

The additive can contain the most dominate chemicals in the hair coloring process. The additive includes the chemicals required to build a chemical screen, raw oxidation dye precursors and couplers and pH modifiers.

The donor hair coloring product can take on many forms but generally will contain the larger basic, direct, oxidation, anionic, ionic, cationic, metallic or acid dye molecules. These dye molecules can vary in size based on shade and condition. The donor hair coloring product also includes many other chemicals such as surfactants, alkali, antioxidants and solvents.

The additive is blended with the donor hair coloring product to form a mixture. The additive holds a pH of 4-7 and the donor hair coloring product holds a higher pH, dependent on the type. The additive chemicals are drawn into the donor through ionic attraction. The chemicals within the donor will act as a catalyst for the chemical screen and, in most cases, it will be through a hydrolysis action.

All hair dye molecules are now blended into the mixture. The pH drops to a neutral range by the dilution of its cationic chemicals, combined with the introduction of additional antioxidants from the additive. A solvent may be added to control viscosity. The chemical screens begin to build and grow in physical size or disperse evenly if in a granular form. A chemical hair coloring mixture has now been produced.

Timing is a key concern when the chemical hair coloring mixture is produced, because the chemical screens continue to grow in size and the dye molecules have been disrupted. The pH may begin to rise, dependent on the donor type. The chemical screen forms around the dye molecules thus encasing them. The dye molecules are now considered to be on the inside of the chemical screen waiting to be transported.

The condition of the hair shaft plays a vital role in the hair coloring process. It is best practice to maintain a negative or anionic charge on or in the hair shaft. This negative charge combined with the wicking effect of dry hair will become the mechanical means to draw the mixture towards the hair shaft.

A third chemical component may optionally be added to the mixture and this will determine the final classification of hair coloring product created. In the case of permanent hair coloring, an oxidizer is added to the mixture and blended thoroughly. The mixture must now be applied to the hair shaft immediately as a chemical reaction is taking place. If an oxidant is used, it's more dramatic and for the purpose of teaching the art we will use this example here forward.

Once the mixture is combined with an oxidizer, it is applied to the hair shaft and the hair coloring process begins. The oxidizer greatly increases pH and adds a cationic charge to the mixture. When a proper viscosity is reached, the chemicals within the mixture begin to travel or transport towards the hair shaft induced by an opposite electrical draw combined with capillary action.

The liquid consistency of the mixture will soften the hair shaft and the alkali will open the cuticle scales to an optimal range of 10 angstrom or less. The oxidizer will reach the hair shaft first and begin the process of dissolving the intercellular matter followed by dissolving the cortical cell walls and finally dissolving the melanin and dye pigments found in the pigment cavities. Once all this matter is dissolved it naturally flows out of the hair shaft leaving behind voids, pockets or cavities lacking any matter.

The process in which these cavities are filled is the focal point behind creating a custom hair color tone that is considered premium and permanent. The invention uses a unique method to do such as all the mechanical functions of the invention begin to perform as intended.

Presently, all the hair color dye molecules are on the inside of the chemical screen within the mixture. The chemical screen reaches its optimal size of over 200,000 u and a precise mesh opening has been determined. In this example, the mesh opening can be set to screen dye molecules 6 angstrom and over.

All chemicals within the mixture are drawn towards the hair shaft and the first point of contact is the cuticle. The chemical screen is physically larger than the optimal 10 angstrom or less opening in the cuticle scales so it remains on the outside while smaller chemical molecules are allowed to pass through the chemical screen.

The oxidation dye molecules from the additive are designed to be the fastest traveling molecules because they are the smallest and most pure. Most dye molecules from the additive will range from 4-6 angstrom in size so they will pass through the chemical screen first followed by the smallest dye molecules from the donor hair coloring product.

Once these dye molecules reach the cuticle scales, they will travel through one of two paths. The first path is the faster intercellular route and the second path is the transcellular route. This first dye molecules to reach the pigment cavities are the smallest and the lightest shades. They hold the ability to fill the smallest cavities within the pigment cavities and cortical cells.

The second dyes to reach the pigment cavities are the small dye molecules that took the transcellular route and since they took the slower route, they will be slightly larger in molecular size but tend to retain their lighter shades of color.

As the physical size of dye molecules passing through the chemical screen increases their progression or flow rate decreases and the third dyes to reach the cortex are the midsized dyes that may contain direct dyes or oxidation dyes or any combination of them. These shades tend to be middle shades.

The next dyes to pass through the chemical screen are the larger dye molecules that are up to 6 angstrom in size. These dyes are forced to travel the intercellular route and attempt to fill the pigment cavities. If already filled by other dyes, they will fill the cavities within the cortical cell. These dye molecules may be oxidation dyes or any blend of dyes capable of physically passing all barriers. These dye shades will be darker but may contain a mixture of all shades.

The last dyes to reach the cortex will be the dye molecules that are sized over 6 angstrom. The chemical screen has attempted to restrict the flow of these large dye molecules and the cuticle scales will add a secondary physical screen in which to pass but eventually some will pass. Most cavities will be filled within the cortical cell by other smaller dye molecules so these large dye molecules will fill the non-keratin zone of the cuticle. These dye molecules can be a blend of all types and generally will be the darkest shades.

The chemicals within the additive can include an alkali or acidifier intended to control the pH level at the cuticle scale location. This balancing of pH will determine the width the cuticle scales open. It is possible to create a secondary physical dye molecule screen by controlling the opening width of the cuticle scales to align directly with the size of dye molecule intended to pass.

Regardless of the dye types and shades delivered to the cortex it will only accept so much before it is considered full. Oxidation dyes are unique whereas they grow physically in size as they transform through the di, tri and polynuclear phases. This dye transformation process forces a reverse physical action that begins to push dye molecules out of the cortex. This reverse force dislodges and pushes the chemical screens away from the cuticle opening thus cleaning it and once the hair is washed with water the pH will drop and the cuticle scales will close completely.

The above represents a preferred dye diffusion process where the goal is to fill every cavity within the cortex with hair dye. This can only be done by depositing smaller dye molecules first followed by molecules of larger size in graduation to ultimately form a layered effect.

Safety is an important concern, and the additive is developed to lower the toxicity level of chemicals used in the hair coloring process. Lower toxicity is achieved in two steps: (1) The additive holds the ability to produce a more refined and potent hair coloring solution when blended with the donor so less donor product will be required in the mixture. A typical donor product's performance level can be increased by three times. (2) The additive targets toxic residues left behind after the hair coloring process by either dismantling them or encapsulating them.

An important factor in the disclosed hybrid hair dye (containing the additive and the donor) is electrical polarity. Many electrons and ions of both positive and negative charge are present in the additive chemical formula. The manipulation of these electrical charges is an important consideration that impacts how well the chemical formulation performs. The polarity of the additive is altered in a phased approach where one polarity may dominate in a stable condition and be altered by mixing the additive with the donor to switch its polarity, assisting with the dye diffusion process.

Color Tone

The art of creating a precise single color shade from all the variables stated within this disclosure was a major undertaking. There are three components that contain color shades. The first is the additive, the second is the donor hair coloring product and the third is the hair shaft. The additive contains raw oxidation dye molecules and the donor may include any combination of basic, direct, oxidation, anionic, ionic, cationic, metallic and acid dye molecules. The hair shaft contains natural melanin and previously applied hair dyes.

There are a variety of additive formulas, and each can be visually identifiable. Each version of the additive can be packaged as a single dose that aligns with a precise volume of donor product. As an example, 30 g of donor product directly aligns with a 5 g or less dose of additive. There are many variables and many possible additive/donor combinations can be produced.

The disclosure includes a calculating system to assist with combining the correct additive dose with the correct donor product. A manual or electronic chart gathers all the data relevant to the hair color process, calculates this data and provides a sum that is equal to a specific single or multiple doses of additive.

The data gathered can include the condition of a client's hair, current color shade, prior hair coloring services used, allergies, amount of grey hair and final expected color shade desired. A donor product is selected based on quality and affordability and this data is entered. Any miscellaneous information such as a time restriction can also be gathered.

Each piece of data gathered is assigned a number or identifying mark, where an example is an allergy is assigned a certain number or mark, amount of grey is assigned a certain number or mark and the expected color shade is assigned a number or mark. The donor type is also assigned a certain number or mark and any additional miscellaneous data is assigned a number or mark. A manual chart or electronic calculating system uses a mathematical formula to produce a sum from all the entered numbers or marks.

The additive known as the invention is considered the engine or apex of the hair coloring process. It includes the precise blend of oxidation dye precursors and couplers, the chemical screen components, pH balancing ingredients and electronic influencing chemicals.

The dye diffusion method of the invention is combined with the chemicals within the additive to create a single color shade within the cortex of the hair shaft. All color shades are a combination of the three primary colors: red, yellow and blue in some proportion.

The additive includes a blend of dye precursors and couplers to create the lightest tri-color segment or hue of the color formula. If this lightest shade is very small in proportion, the additive may include an additional blend of dye precursors or couplers that create the second segment or hue of the hair coloring formula.

The donor may include multiple types and shades of hair dyes. The middle shades or darker shades of the tri-color formula may be drawn from the donor product. There are several variables in color tone options and most are dictated by the size of the dye molecule. An example is a light basic dye molecule is much larger than a light direct dye molecule.

The hair shaft most often holds melanin or dye remnants from prior hair services. This must be accounted for because these color shades will blend with these dyes, changing or influencing the final color shade effect.

Each precise single color tone produced within the cuticle is a tri-color combination of dyes or melanin sourced from three locations. These dye types may also vary whereas tan melanin (A) can be combined with a red oxidation dye (B) and a second blue oxidation dye (C) or a brown oxidation dye (A) can be combined with a green direct dye (B) and a yellow basic dye (C).

The disclosure provides an endless number of combinations that can be used to create a precise single color tone. These custom color shades permanently attach to the hair shaft and the structure of the hair shaft is restored to produce a perfect shine and strength.

The additive and donor hair coloring product can share some common ingredients but the way that they are used and packaged makes these two products opposites of one another. The donor hair coloring product is a commercially prepackaged hair coloring solution capable of producing a desired change in hair color tone. All of the chemical ingredients required are included and blended into a single formula that is then applied by the applicator.

The additive is a small non-active blend of hair coloring chemicals intended to deter the forming of a hair coloring solution. Every effort is placed forth to create an atmosphere most unfavorable for hair coloring. The oxygen content is eliminated, the pH is kept at a neutral to acidic range of 4-7, an anionic charge is present and the oxidation dye precursor and couplers are prevented from forming indo dyes.

When the additive is packaged, it can't effectively color hair. Once the additive package is opened, it searches for a catalyst or activating chemicals and, in the case of this invention, it draws them from the donor/additive mixture and the donor gives to the acceptor thus producing a workable hair color solution.

Some may try to bypass the use of a donor product and it is possible to activate the additive using other means but it is important to remember that the additive is directly aligned with a donor hair coloring product color shade. This means that the color shade produced will be unfavorable because it only represents a portion of the tri-color balance of basic color theory.

Methods

FIG. 1 is a method of applying the additive of this disclosure. The method begins with Step 1 10, which is providing an additive consisting essentially of: a substance or formula added to another in relatively small amounts to effect a desired change in properties, consisting essentially of: a chemical formula with a pH of 4 to 7; at least one oxidation dye precursor and/or oxidation dye coupler; an excipient; the additive configured to align directly with a donor hair coloring product; and the additive lacking either the chemical components or atmospheric conditions necessary to effectively color hair. Step 2 11 is providing a donor hair coloring product comprising: a chemical compound capable of giving up a part for combination with an acceptor, comprising: an existing commercial hair coloring product or chemical formulation configured to color hair, comprising: at least one of a surfactant, a carrier solution or solvent; at least one of an alkali, an antioxidant, a reducing agent, or a carrier solution; and at least one basic, direct, oxidation, anionic, ionic, cationic, metallic or acid dye molecule; the additive and donor hair coloring product each containing hair dye; wherein the acceptor comprises the additive; wherein the additive and the donor hair coloring product are configured to regulate or meter the flow rate of dye molecules based on molecular size. Step 3 12 is mixing the additive and donor hair color product together to create a mixture containing hair dye molecules sourced from the additive and hair dye molecules sourced from the donor hair coloring product. Step 4 13 is applying the mixture to a hair shaft to alter the hair shaft's perceived color.

The method of FIG. 1 can optionally include the method steps shown in FIG. 2. In Step 3a 14, an oxidizer can be added to the mixture prior to applying the mixture to the hair shaft. In Step 3b 15, it is optional to generate a chemical screen or matrix in the mixture to block or meter hair dye molecules and to place them within the hair shaft in order of increasing molecular size. Step 4 13 can optionally include coloring the hair, using the mixture, to utilize three sources of color: the hair dye molecules of the additive, the hair dye molecules of the donor hair product and the melanin or residual dyes from the existing hair shaft to generate a precise hair color tone. The method can optionally include Step 4a 16, which is encapsulating toxic residues, through the mixture, after the hair coloring process is complete. In Step 2a, the method can include: collecting data comprising: the condition of a client's hair; the client's current color shade; prior hair coloring services received by the client; known allergies of the client; the amount of gray hair in the client's hair; and the final expected color shade desired by the client; using the data collected to select a donor hair coloring product; assigning each piece of data a number or identifying mark; and using the data collected and the selected donor hair coloring product to determine the additive and the amount of the additive needed to align with the donor hair coloring product using a mathematical formula.

FIGS. 3A & 3B together are a method of creating a single-color tone in a hair shaft. The method begins in FIG. 3A and extends onto FIG. 3B. Step 1 20 includes providing an additive consisting essentially of: a substance or formula added to another in relatively small amounts to effect a desired change in properties, consisting essentially of: a chemical formula with a pH of 4 to 7; at least one raw oxidation dye precursor and/or raw oxidation dye coupler; an excipient; the additive configured to align directly with a donor hair coloring product; and the additive lacking either the chemical components or atmospheric conditions necessary to effectively color hair. Step 2 21 includes providing a donor hair coloring product comprising: a chemical compound capable of giving up a part for combination with an acceptor, comprising: an existing commercial hair coloring product or chemical formulation configured to color hair, comprising: at least one of a surfactant, a carrier solution or solvent; at least one of an alkali, an antioxidant, a reducing agent, or a carrier solution; and at least one basic, direct, oxidation, anionic, ionic, cationic, metallic or acid dye molecule; the additive and the donor hair coloring product each comprising hair dye; wherein the acceptor comprises the additive; and wherein the additive and the donor hair coloring product are configured to regulate or meter the flow rate of dye molecules based on molecular size. Step 3 22 includes blending the additive and donor hair coloring product to create a mixture, wherein the mixture contains a ratio of the active component of the additive to the donor hair coloring product of less than 3:20 by volume or weight. Step 4 23 includes the oxidation dyes precursors and oxidation dye couplers of the additive forming at least single nuclear indo dyes. Step 5 24 includes creating, in the mixture, chemical screens ranging from 200,000 u to 800,000 u in molecular mass and configured to encapsulate and meter the flow rate of hair dye molecules over 6 angstrom. Step 6 25 includes maintaining a pH level of 6-8 in the mixture and Step 7 26 includes adding an oxidizer to the mixture. Step 8 27 includes establishing a pH level of neutral to acidic on a client's hair, and Step 9 28 includes applying the mixture to a user's hair, the mixture softening the hair shaft, an alkali opening the user's hair cuticle scales to a width of about 10 angstrom or less using a pH level of 7 to 10. Step 10 29 includes dissolving the user's hair intercellular matter and cortical cell walls to reach the pigment cavities using the mixture, dissolving natural melanin and/or residual hair dyes in the hair shaft. Step 11 30 includes forcing the dissolved matter out of the hair shaft, using the mixture; leaving a network of holes, voids and cavities in the hair shaft, and configuring the hair shaft to accept new hair dye. Step 12 31 includes chemically, physically or electronically transporting the mixture, through the chemical screen or filter, and Step 13 32 includes chemically, physically or electronically transporting the mixture, through the chemical screen or filter. Step 14 33 includes reaching the cuticle of the hair shaft and penetrating it using either the transcellular or intercellular route; filling the network of holes, voids and/or cavities in the hair shaft with hair dyes, sourced from both the additive and from the donor hair coloring product; and wherein the filling is configured to occur in a layered effect based on the size of hair dye molecules, passing through the chemical screens.

Figure 4:
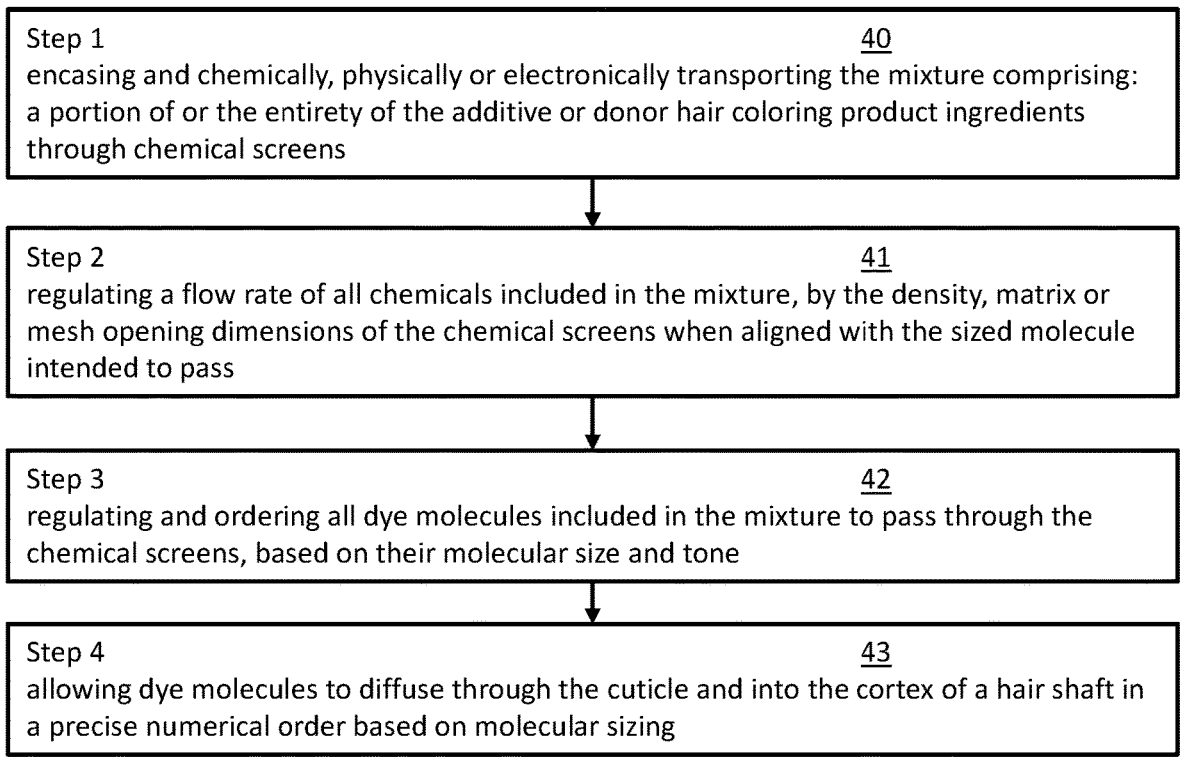
FIG. 4 is a method of chemically screening hair dyes that can be used with the method of creating a single-color tone in a hair shaft shown in FIGS. 3A & 3B or used independently.

FIG. 4 is a method of chemically screening hair dyes that can be used with the method of creating a single-color tone in a hair shaft shown in FIGS. 3A & 3B or as an independent method. In the method of chemically screening hair dyes, Step 1 40 includes encasing and chemically, physically or electronically transporting the mixture comprising: a portion of or the entirety of the additive or donor hair coloring product ingredients through chemical screens. Step 2 41 includes regulating a flow rate of all chemicals included in the mixture, by the density, matrix or mesh opening dimensions of the chemical screens when aligned with the sized molecule intended to pass. Step 3 42 includes regulating and ordering all dye molecules included in the mixture to pass through the chemical screens, based on their molecular size and tone. Step 4 43 includes allowing dye molecules to diffuse through the cuticle and into the cortex of a hair shaft in a precise numerical order based on molecular sizing.

What has been described is an additive for use with donor hair coloring products to produce a precise color tone within the hair shaft. In this disclosure, there are shown and described only exemplary embodiments of the invention, but, as aforementioned, it is to be understood that the invention is capable of use in various other combinations and environments and is capable of changes or modifications within the scope of the inventive concept as expressed herein.

From the foregoing disclosure and detailed description of certain preferred embodiments, it is also apparent that various modifications, additions and other alternative embodiments are possible without departing from the true scope and spirit. The embodiments discussed were chosen and described to provide the best illustration of the principles of the present invention and its practical application to thereby enable one of ordinary skill in the art to utilize the invention in various embodiments and with various modifications as are suited to the particular use contemplated. All such modifications and variations are within the scope of the present invention as determined by the appended claims when interpreted in accordance with the benefit to which they are fairly, legally, and equitably entitled.

TABLE 1

Inclusive list of exemplary antioxidants or inert medium appropriate for the additive:

| Antioxidants | Inert Medium |
|---|---|
| Sodium Sulfite | Nitrogen |
| Sodium Metabisulfite | Carbon Dioxide |
| Ascorbic Acid | Helium |
| Tocopherols | Neon |
| Poropyl Gallate | Argon |
| Tertiary Butylhydroquinone | Hydrogen |
| Butylated Hydroxyanisole | Radon |
| Butylated Hydroxytoluene | Xenon |
| Vitamin A | Krypton |
| Vitamin E | |
| Vitamin C | |
| Retinyl Palmitate | |
| Citric Acid | |
| Cysteine | |
| Methionine | |
| Sodium Citrite | |
| Methyl Paraben | |
| Propyl Paraben | |
| BHT | |

TABLE 2

Inclusive list of exemplary reducing agents appropriate for the additive:

Ammonium Sulfite
Decapeptide-7
Oligopeptide-30
Formic Acid
Oxalic Acid
Sulfite
Nascent Hydrogen
Hydrogen
Sodium Amalgam
Zinc
Diborane
Sodium Borohydride
Sulfate
Chloride
Sulfur Dioxide
Dithionates
Thiosulfates
Iodides
Hydrogen Peroxide
Hydrazine
Disobutylaluminium Hydride
Ascorbic Acid
Carbon
Sodium TABLE 2-continued Inclusive list of exemplary reducing agents appropriate for the additive:

Magnesium
Aluminum
Lithium Aluminum Hydroxide
Red-Al
Barium
Calcium
Potassium

TABLE 3

Inclusive list of exemplary excipients appropriate for the additive:

Calcium Palmitate
Magnesium Stearate
Fumed Silica
Starch
Talc
Ascorbyl Palmitate
Calcium Palmitate
Cornstarch
Colloidal Silica
Dl-leucine
Sodium Lauryl Sulfate
Stearates
Polyvinylpyrolidone
Polyethylene Glycol
Saccharides
Polysaccharides
Petrolalum
Dimethyl Sulfoxide
Mineral Oil
Desiccants
Amorphous Silica
Cab-o-Sil ®
Aerosil ®
Mannitol
Silicon Dioxide
Polyacrylamide
Quarternized Hydroxyethyl
Polyacrylic Acid
Quarternized Copolymer
Polymides
Silicone Plymers
Polymeric Cationic Cellulose
Dimethiconol
Polyvinyl Pyrolidone
Ethoxylated Ester Polymer
Polyethyleneimine

TABLE 4

Inclusive list of exemplary surfactants appropriate for the additive:

Laureth-2
Oleic Acid
Sodium Laureth-6
Cetearyl Alcohol
Ceteareth-25
Ceteth-2
Cocamide DEA
EDTA
Ethoxydiglycol
Lauramide DEA
Nonoxynol-2
Sodium Lauryl Sulfate
Carboxylic Acid
Sulfates
Sulfonic Acid
Phosphoric Acid
Ammonium Lauryl Sulfate
Taurates
Isethionates TABLE 4-continued Inclusive list of exemplary surfactants appropriate for the additive:

Sodium Dodecyl sulfate
Stearic Acid
Sodium Stearate
Olefin Sulfonates
Sulfosuccinates
Cetrimonium Chloride
Stearalkonium Chloride
Sodium Lauriminodipropionate
Disodium Lauroamphodiacetate
Stearyl Alcohol
Cocamidopropylamine Oxide
Esters
Polysorbate Esters
Aminomethyl Propanol
Hexylene Glycol
Cetrimonium Bromide
Tetradonium Bromide

TABLE 5

Inclusive list of exemplary solvents appropriate for the additive:

Water
Deionized Water
Isopropyl Alcohol
Cetearyl Alcohol
Oleyl Alcohol
Stearyl Alcohol

TABLE 6

Inclusive list of exemplary alkalis and acidifiers appropriate for the additive:

Water
Ammonium Hydroxide
Tartaric Acid
Citric Acid
Triethanol Aminine
Ethanolamine
Monoethanolamine
Para Tolene Diamine
Aminomethyl Propanol
2-Aminoethanol
Ethylene Glycol
Propylene Glycol
Triethylene Glycol
Acetic Acid
Acetonitrile
Triethylphosphate
Dimethyl Formamide
Diethylene Glycol Monomethylether
Monoethanolamine

TABLE 7

Inclusive list of exemplary oxidation dye precursors and oxidation dye couplers appropriate for the additive and donor hair coloring product:

| Oxidation Dye Precursors | Oxidation Dye Couplers |
| --- | --- |
| p-phenylenediamene | resorcinol |
| o-amino phenol | 1-naphthol |
| 2,4 diamino phenoxyethanol | 2-methylresorcinol |
| 4-methylaminophenol | 3-methylamino-4-nitro-phenoxyethanol |
| 4-amino-m-cresol | 4-amino-2-hydroxytoluene |
| 4-nitro-o-phenylenediamine | m-amino phenol |
| 2-amino-3-hydroxypyridine | |
| 2,4 Diaminophenol | 1,5-naphthalenedoil |
| 2-Methoxy-p-phenylenediamine | 1,2,4 Trihydroxybenzene |

TABLE 7-continued

Inclusive list of exemplary oxidation dye precursors and oxidation dye couplers appropriate for the additive and donor hair coloring product:

| Oxidation Dye Precursors | Oxidation Dye Couplers |
| --- | --- |
| Toluene-2,5-diamine | 3,4 Dihydroxyaniline |
| 2-Chloro-p-phenylenediamine | m-Phenylenediamine |
| n-Phenyl-p-phenylenediamine | 2,4-Diaminophenoxyethanol |
| Hydroxyethyl-p-phenylenediamine | 2-Amino-4-hydroxyewthylaminoanisole |
| | 2,6-Diaminopyridine |
| n,n-bis-Phenylenediamine | 2,6-Diaethoxy-3,5-pyridinediamine |
| 6-Amino-m-cresol | 2,6-Dihydroxyethuylaminotoluene |
| p-Aminophenol | m-Aminophenol |
| p-Methylaminophenol | 4-Amino-2-hydroxytoluene |
| n-2-Hydroxyethyl-4-aminophenylamino | 2-Methyl-5-Hydroxyethylaminophenol |
| | 3-Amino-2,4-dichlorophenol |
| 2,4,5,6-Tetraminopyrimidine | 5-Amino-6-chloro-o-cresol |
| Bridged Precursors (combinations) | 4-Chlororesorcinol |
| | Hydroquinone |
| | 1-Acetoxy-2-methylnaphthalene |
| | p-Aminophenol |
| | 4-Amino-2-methylphenol sulfate |
| | 4-Amino-3-methylphenol |
| | 4-Amino-2-nitrophenol |
| | 2,4-Diaminophenol hydrochloride |
| | 4-Chloro-2-aminophenol |
| | 4-Nitro-2-aminophenol |
| | 4,6,-Dinitro-2-aminophenol |
| | 6-Chloro-4-nitro-2-aminophenol hydrochloride |
| | o-Phenylenediamine |
| | p-Toluylenediamine |
| | o-Toluylenediamine |
| | 3,4-Toluylenediamine |
| | Choloro-p-phenylenediamene sulfate |
| | 4-Choloro-o-phenylenediamene sulfate |
| | 4-Nitro-o-phenylenediamine |
| | 5-Choloro 3-nitro o-phenylenediamine |
| | 1,2,4,Triaminobenzene dihydrochloride |
| | p-Aminodimethylaniline |
| | p-Aminodiphenylamine |
| | 4-Aminodiphenylamine |
| | 2,4,Diaminodiphenylamine |
| | 4,4,Diaminodiphenylamine |
| | 2-Aminodiphenylamine |
| | 4-Methoxy-4-amino-diphenylamine sulfate |

TABLE 8

Inclusive list of exemplary oxidation dye coupler alternatives appropriate for the additive:

Trifluoroalkyl
Ether
Alkylsulfonamides
Aromatic Acid
Heterocyclic Acid
Heteroaromatic Acid
Amino Acid
Halogens

What is claimed is:

1. An additive directly aligned to a donor hair coloring product, consisting essentially of:
   an additive consisting essentially of:
      a substance or formula added to another in relatively small amounts to effect a desired change in properties where the substance or formula has a pH of 4 to 7, consisting essentially of:
   at least one oxidation dye precursor and/or oxidation dye coupler;
   an excipient;

the additive configured to align directly with a donor hair coloring product; and
the additive lacking either the chemical components or atmospheric conditions necessary to effectively color hair;
wherein the additive is directly aligned with a donor hair coloring product comprising:
a chemical compound capable of giving up a part for combination with the additive, comprising:
an existing commercial hair coloring product or chemical formulation configured to color hair, comprising:
at least one of a surfactant, a carrier solution or solvent;
at least one of an alkali, an antioxidant, a reducing agent, or a carrier solution; and
at least one basic, direct, oxidation, anionic, ionic, cationic, metallic or acid dye molecule;
wherein the additive is proportionately aligned to the donor hair coloring product to create a custom hair coloring solution with hair dyes sourced from both the additive and the donor hair coloring product to create a single color shade; and
wherein the additive is configured to regulate or meter the flow rate of dye molecules based on molecular size.

2. The additive of claim 1, the additive comprising active and/or non-active chemical components wherein the active chemical compounds promote chemical activity and the non-active chemical components deter, prevent or limit chemical activity; and wherein the additive and the donor hair coloring product are performance dependent.

3. The additive of claim 2, wherein the hair coloring solution comprises a ratio of the active component of the additive to the donor hair coloring product of less than 3:20 by volume or weight.

4. The additive of claim 3, wherein no active component of the additive in a ratio to the donor hair coloring product, is greater than 1:10 by volume or weight.

5. The additive of claim 4, wherein the additive is configured to chemically react with the donor hair coloring product to chemically transform a portion of the additive into chemical screens configured to screen and filter dye molecules based on size.

6. The additive of claim 5, wherein the additive is configured to chemically use the donor hair coloring product to chemically build at least one excipient into the chemical screens.

7. The additive of claim 5, wherein the additive's excipient, holding a pH of 4-7 and a neutral to anionic charge, is configured to be mixed with a donor hair coloring product, holding a pH of greater than 7 and a cationic charge, and configured to draw excipients out of the additive and activating them and causing chemical screens to be constructed.

8. The additive of claim 5, wherein a mixture of the additive and the donor hair coloring product comprises particulates or granules dispersed evenly throughout the mixture to perform as physical dye chemical screens.

9. The additive of claim 5, wherein a mixture of the additive and the donor hair coloring product is configured to cause a catalyst to be drawn out of the donor hair coloring product or added to the mixture to grow polymeric chemical screens in one of a fractal, linear or branched chain of repeating units fixed together via chemical links to form a restrictive barrier or matrix.

10. The additive of claim 5, wherein a mixture of the additive and the donor hair coloring product is configured to direct some hair dye molecules through a transcellular route and other hair dye molecules through an intercellular route through the cuticle layer of human hair.

11. The additive of claim 10, wherein the mixture is configured to custom build a color tone within a hair shaft based on precise dye placement based on molecular size and tone.

12. The additive of claim 11, wherein the mixture is configured to use capillary action and/or electrochemical action to draw the hair dye molecules into cortex cavities of the hair shaft in a numerical order based on physical molecular size.

13. The additive of claim 12, wherein the mixture is configured to dismantle, salvage and/or encapsulate portions of the donor hair coloring product.

14. A method of coloring hair, steps comprising:
providing an additive consisting essentially of:
a substance or formula added to another in relatively small amounts to effect a desired change in properties where the substance or formula has a pH of 4 to 7, consisting essentially of:
at least one oxidation dye precursor and/or oxidation dye coupler;
an excipient;
the additive configured to align directly with a donor hair coloring product; and
the additive lacking either the chemical components or atmospheric conditions necessary to effectively color hair;
providing a donor hair coloring product comprising:
a chemical compound capable of giving up a part for combination with the additive, comprising:
an existing commercial hair coloring product or chemical formulation configured to color hair, comprising:
at least one of a surfactant, a carrier solution or solvent;
at least one of an alkali, an antioxidant, a reducing agent, or a carrier solution; and
at least one basic, direct, oxidation, anionic, ionic, cationic, metallic or acid dye molecule;
the additive and donor hair coloring product each containing hair dye;
wherein the additive and the donor hair coloring product are configured to regulate or meter the flow rate of dye molecules based on molecular size;
mixing the additive and donor hair color product together to create a mixture containing hair dye molecules sourced from the additive and hair dye molecules sourced from the donor hair coloring product; and
applying the mixture to a hair shaft to alter the hair shaft's perceived color.

15. The method of claim 14, wherein the steps comprise:
encapsulating toxic residues, through the mixture, after the hair coloring process is complete.

16. The method of claim 14, wherein the steps comprise:
adding an oxidizer to the mixture prior to applying the mixture to the hair shaft; and
coloring the hair, using the mixture, to utilize three sources of color: the hair dye molecules of the additive, the hair dye molecules of the donor hair product and the melanin or residual dyes from the existing hair shaft to generate a precise hair color tone.

17. The method of claim 16, wherein the steps comprise:
generating a chemical screen or matrix in the mixture to block or meter hair dye molecules and to place them within the hair shaft in order of increasing molecular size.

18. The method of claim 15, wherein the additive comprises a containment package comprising a dose of the additive.

19. The method of claim 16, wherein the steps comprise:
collecting data comprising:
the condition of a client's hair;
the client's current color shade;
prior hair coloring services received by the client;
known allergies of the client;
the amount of gray hair in the client's hair; and
the final expected color shade desired by the client;
using the data collected to select a donor hair coloring product;
assigning each piece of data a number or identifying mark; and
using the data collected and the selected donor hair coloring product to determine the additive and the amount of the additive needed to align with the donor hair coloring product using a mathematical formula.

20. The method of claim 18, wherein the containment package contains a dose of the additive and an inert gas.

21. The method of claim 20, wherein the additive containment package contains a dose of additive that is less than 3:20 by volume or weight compared with the aligned donor hair coloring product.

22. A method of applying a hair coloring solution to generate a precise color tone, steps comprising:
providing an additive consisting essentially of:
a substance or formula added to another in relatively small amounts to effect a desired change in properties where the substance or formula has a pH of 4 to 7, consisting essentially of:
at least one raw oxidation dye precursor and/or raw oxidation dye coupler;
an excipient;
the additive configured to align directly with a donor hair coloring product; and
the additive lacking either the chemical components or atmospheric conditions necessary to effectively color hair;
providing a donor hair coloring product comprising:
a chemical compound capable of giving up a part for combination with the additive, comprising:
an existing commercial hair coloring product or chemical formulation configured to color hair, comprising:
at least one of a surfactant, a carrier solution or solvent;
at least one of an alkali, an antioxidant, a reducing agent, or a carrier solution; and
at least one basic, direct, oxidation, anionic, ionic, cationic, metallic or acid dye molecule;
the additive and the donor hair coloring product each comprising hair dye;
wherein the additive and the donor hair coloring product are configured to regulate or meter the flow rate of dye molecules based on molecular size;
blending the additive and donor hair coloring product to create a mixture, wherein the mixture contains a ratio of the active component of the additive to the donor hair coloring product of less than 3:20 by volume or weight;
the oxidation dyes precursors and oxidation dye couplers of the additive forming at least single nuclear indo dyes;
creating, in the mixture, chemical screens ranging from 200,000 u to 800,000 u in molecular mass and configured to encapsulate and meter the flow rate of hair dye molecules over 6 angstrom;
maintaining a pH level of 6-8 in the mixture;
adding an oxidizer to the mixture;
establishing a pH level of neutral to acidic on a client's hair;
applying the mixture to a user's hair, the mixture softening the hair shaft, an alkali opening the user's hair cuticle scales to a width of about 10 angstrom or less using a pH level of 7 to 10;
dissolving the user's hair intercellular matter and cortical cell walls to reach the pigment cavities using the mixture, dissolving natural melanin and/or residual hair dyes in the hair shaft;
forcing the dissolved matter out of the hair shaft, using the mixture;
leaving a network of holes, voids and cavities in the hair shaft, and
configuring the hair shaft to accept new hair dye;
chemically, physically or electronically transporting the mixture, through the chemical screen or filter;
reaching the cuticle of the hair shaft and penetrating it using either the transcellular or intercellular route;
filling the network of holes, voids and/or cavities in the hair shaft with hair dyes, sourced from both the additive and from the donor hair coloring product; and
wherein the filling is configured to occur in a layered effect based on the size of hair dye molecules, passing through the chemical screens.

23. The method of claim 22, wherein the mixture is configured so that the oxidation dyes precursors and or oxidation dye couplers of the additive dominate a hair dye diffusion process.

24. The method of claim 23, wherein the additive's excipient, holding a pH of 4-7 and a neutral to anionic charge, is mixed with a donor hair coloring product, holding a pH of greater than 7 and a cationic charge, drawing excipients out of the additive and activating them and causing chemical screens to be constructed.

25. The method of claim 24, wherein the mixture is configured to cause a catalyst action for the excipient to grow polymeric chemical screens in one of a fractal, linear or branched chain of repeating units fixed together via chemical links to form a chemical chain or matrix.

26. The method of claim 22, wherein the mixture comprises particulates or granules dispersed evenly throughout the mixture and configured to perform as a physical chemical dye screen.

27. The method of claim 22, wherein
the layered effect providing a precise color tone comprises the use of A, B and C shades to create a single color tone;
wherein each of A, B & C shades can be sourced from the additive dye molecules, the donor hair coloring product dye molecules and a color tone existing in the client's hair prior to the application of the mixture.

28. The method of claim 27, wherein
the layered effect providing a precise color tone comprises the step of depositing the A, B & C shades based on dye molecule size, where the additive comprises dye molecules with the lightest shade in the mixture and the donor hair coloring product comprises dye molecules with darker shades in the mixture, causing the light shade additive dye molecules to be deposited before the darker shade donor hair coloring product dye molecules into the hair shaft.

29. The method of claim 28, wherein the A, B & C shades can be any combination of hair dyes in the additive, the donor hair coloring product and melanin from the client's hair.

30. The method of claim 22, steps comprising:
encasing and chemically, physically or electronically transporting the mixture comprising:
a portion of or the entirety of the additive or donor hair coloring product ingredients through chemical screens;
regulating a flow rate of all chemicals included in the mixture, by the density, matrix or mesh opening dimensions of the chemical screens when aligned with the sized molecule intended to pass;
regulating and ordering all dye molecules included in the mixture to pass through the chemical screens, based on their molecular size and tone; and
allowing dye molecules to diffuse through the cuticle and into the cortex of a hair shaft in a precise numerical order based on molecular sizing.

31. The method of claim 30, wherein the chemical screens comprise any single chemical or combination of chemicals that can form a granular or polymeric barrier configured to regulate the passage of other chemicals within a formula or mixture in an orderly fashion, based on molecular size.

32. The method of claim 31, wherein the additive's excipient, holding a pH of 4-7 and a neutral to anionic charge, is mixed with a donor hair coloring product, holding a pH of greater than 7 and a cationic charge, drawing excipients out of the additive and activating them, causing the chemical screens to be constructed.

33. The method of claim 30, wherein a catalyst is drawn out of the donor hair coloring product or added as a separate solvent or surfactant to grow polymeric chemical screens in one of a fractal, linear or branched chain of repeating units fixed together via chemical links to form a chemical screen or matrix.

34. The method of claim 30, wherein particulates and/or granules are dispersed evenly throughout the mixture to create a physical chemical dye molecule screen.

35. The method of claim 30, wherein the chemical screens are built using chemicals capable of polymerization.

36. The method of claim 30, wherein the chemical screens are built to a size of at least 200,000 u to 800,000 u to prevent their penetration through the cuticle cells or their openings thus forcing all chemicals to pass through the chemical screens before entering the cortex of the hair shaft.

* * * * *